(12) United States Patent
Buckley et al.

(10) Patent No.: US 9,180,089 B2
(45) Date of Patent: Nov. 10, 2015

(54) COMPOSITIONS AND METHODS FOR INDUCING OR ENHANCING CONNECTIVE TISSUE REPAIR

(75) Inventors: Peter Byron Buckley, Uppsala (SE); Konrad Messmer, Munich (DE); Mark William Phillips, Coconut Creek, FL (US)

(73) Assignee: GLenpharma AB, Uppsula (SE)

( * ) Notice: Subject to any disclaimer, the term of this patent is extended or adjusted under 35 U.S.C. 154(b) by 0 days.

(21) Appl. No.: 13/496,933

(22) PCT Filed: Sep. 21, 2010

(86) PCT No.: PCT/US2010/049640
§ 371 (c)(1),
(2), (4) Date: Mar. 19, 2012

(87) PCT Pub. No.: WO2011/037912
PCT Pub. Date: Mar. 31, 2011

(65) Prior Publication Data
US 2012/0177600 A1 Jul. 12, 2012

Related U.S. Application Data

(60) Provisional application No. 61/272,427, filed on Sep. 23, 2009.

(51) Int. Cl.
| | | |
|---|---|---|
| A61P 37/06 | (2006.01) |
| A61P 17/00 | (2006.01) |
| A61P 29/00 | (2006.01) |
| A61K 31/726 | (2006.01) |
| A61K 31/727 | (2006.01) |
| A61K 38/20 | (2006.01) |
| A61P 25/00 | (2006.01) |
| A61K 31/721 | (2006.01) |
| A61K 38/18 | (2006.01) |
| A61P 19/04 | (2006.01) |
| A61P 7/02 | (2006.01) |
| A61K 31/728 | (2006.01) |
| A61P 9/10 | (2006.01) |
| A61K 31/718 | (2006.01) |
| A61K 31/715 | (2006.01) |
| A61K 9/00 | (2006.01) |
| A61K 45/06 | (2006.01) |

(52) U.S. Cl.
CPC ............. *A61K 9/0019* (2013.01); *A61K 31/715* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 4,521,252 A | * | 6/1985 | Miyake et al. ............... | 127/46.3 |
| 4,716,154 A | * | 12/1987 | Malson et al. ................ | 514/54 |
| 5,358,973 A | * | 10/1994 | Lindblad et al. ............. | 514/777 |
| 5,902,800 A | | 5/1999 | Green et al. | |
| 6,303,585 B1 | * | 10/2001 | Spiro et al. ..................... | 514/54 |
| 2003/0130205 A1 | * | 7/2003 | Christian ........................ | 514/23 |
| 2008/0025950 A1 | | 1/2008 | Prestwich et al. | |
| 2008/0268024 A1 | | 10/2008 | Prous et al. | |
| 2009/0042834 A1 | | 2/2009 | Karageozian et al. | |
| 2009/0124540 A1 | | 5/2009 | Prestwich et al. | |

FOREIGN PATENT DOCUMENTS

WO   WO 2008156354 A1 * 12/2008

OTHER PUBLICATIONS

Ogawa,T; et al; "Natural killer cell activities of synbiotic *Lactobacillus casei* ssp. casei in conjunction with dextran" Clincal and Experimental Immunology, 143, 103-109, 2005.*
International Search Report and Written Opinion for PCT/US2010/049640 mailed Nov. 8, 2010 (10 pages).
International Preliminary Report on Patentability for PCT/US2010/049640 dated Dec. 13, 2011 (9 pages).
Dyson S.J., Treatment of superficial digital flexor tendinitis: A comparison of conservative management, sodium hyaluronate . . . , AAEP Proceedings; vol. 43, 297-300, 1977.
Dyson S.J, Medical Management of Superficial Digital Flexor Tendonitis: A Comparative Study in 219 horses (1992-2000) Equine Veterinary Journal 2004; 36: 415-419.
Williams et al., Development of collagen fibril organization and collagen crimp patterns during tendon healing, Int. J. of Biol. Macro. vol. 7, Issue 5, Oct. 1985 (275-282).
Neuss S., et al., Secretion of fibrinolytic enzymes facilitates human mesenchymal stem cell invasion into fibrin clots. Cells Tissues Organs. 191(1):36-46, Apr. 24, 2009.
Salter, et al., Platelets modulate ischemia/reperfusion-induced leukocyte recruitment in the mesenteric circulation. Am. J. Phys. Gastro. Liver Phys. Dec. 2001; 281(6):G1432-9.
Croner RS, et al. Hepatic platelet and leukocyte adherence during endotoxemia. Crit Care Feb. 2006;10(1):R15, pp. 1-6.
Olutoye OO, et al. Hyaluronic acid inhibits fetal platelet function: implications in scarless healing. J. Pediatr Surg. Jul. 1997; 32(7):1037-40.
Strauss RG, et al., Effects of hydroxyethyl starch on fibrinogen, fibrin clot formation, and fibrinolysis. Transfusion. vol. 25, Issue 3, pp. 230-234, May-Jun. 1985.
Carr, M. et al., Fibrin structure and concentration alter clot elastic modulus but do not alter platelet mediated force development. Blood Coag. & Fib. 6(1):79-86, Feb. 1995.
Arfors K E, et al., Pharmacological characteristics of artificial colloids. (1997) Bailliere's Clinical Anaesthesiology, 11 (1), pp. 15-47.
Steinbauer M, et al., Effects of dextran on microvascular ischemia-reperfusion injury in striated muscle. Am. J. Physiol. 272: H1710-H1716, 1997.
Steinbauer M, et al., Impact of dextran on microvascular disturbances and tissue injury following ischemia/reperfusion in striated muscle. Shock, 9, 5, 345-351, 1998.
Stashak T S, (ed) Adams' Lameness in Horses 5th Edition, pp. 612-617 Publisher: Lippincott, Williams & Wilkins (Jun. 2002).
Boilard E., et al., Platelets amplify inflammation in arthritis via collagen-dependent microparticle production. Science, 2010, Jan. 29: 327(5965): 580-3, (10 pages).

(Continued)

*Primary Examiner* — Blaine Lankford
*Assistant Examiner* — David Berke-Schlessel
(74) *Attorney, Agent, or Firm* — Taft Stettinius & Hollister LLP; Ryan O. White

(57) ABSTRACT

A composition capable of attenuating platelet hyperactivation and associated methods for administering the same to a subject, the composition comprising an aqueous solution containing from about 0.1% to about 7.0% by weight of a glycosaminoglycan and from about 1.0% to about 32% by weight of a neutral polysaccharide.

5 Claims, No Drawings

(56) References Cited

OTHER PUBLICATIONS

Dowling, et al. Superficial Digital Flexor Tendonitis in the Horse. Equine Veterinary Journal 2000; 32: 369-378.

Ross MW, Dyson SJ, Superficial Digital Flexor Tendonitis, IN: Ross MW, Dyson SJ, eds Diagnosis and Management of Lameness in the Horse, St. Louis: Saunders, 2003; 628-643.

Silver, et al.; A Clinical and Experimental Study of Tendon Injury, Healing and Treatment in the Horse. Equine Veterinary Journal Supplement 1983; 1: 1-42.

Davis, et al., Diagnosis and Management of Tendon and Ligament Disorders. In: Aver JA, Stick JA, eds. Equine Surgery 3rd edition St. Louis: Saunders, 2006; 1086-1111.

Chesen AB, et al. Tendonitis of the Proximal Aspect of the Superficial Flexor Tendon in Horses: 12 cases (2000-2006) JAVMA Jun. 1, 2009, vol. 234, No. 11 1432-1436.

Green, et al., The Inhibition of Flexor Tendon Adhesions. Bull Hosp JT Dis Orthopedic Institute; 1986 Spring; 46 (1); 16-21.

Robinson RJ, et al., The Annals of Thoracic Surgery, vol. 37, No. 6 Jun. 1984, pp. 488-490.

Eriksson, et al.; Effect of Dextran on Plasma Tissue Plasminogen Activator (T-PA) and Plasminogen Activator Inhibitor-1 (PAT-1) . . . Acta Anes. Scand. Feb. 1995; 39 (2) 163-166.

Smith, et al., Ultronographic Imaging of the Flexor Tendons in a Clinical Context. Proc. of the 10th Inter. Cong. of World Equine Veterinary Ass., Jan. 28-Feb. 1, 2008, 269-273.

Dubick, M.A., et al., AD-A250 421; 92-12378—Dextran Metabolism Following Infusion of 7.5% NaCl/6% Dextran-70 to Euvolemic and Hemorrhaged Rabbits—Drug Development Research 25:29-38 (1992).

Chytil, F., et al., Institute of Physiology, Czechoslovak Academy of Sciences and Institute of Haematology and Blood Transfusion, Prague, Czechoslovakia—An Enzyme Splitting Dextran in Dog Serum; Blut, Band XII, Seite 310-313 (1966).

Arond, L.H., et al., Institute of Polymer Research, Polytechnic Institute of Brooklyn, Brooklyn, N.Y.; Molecular Weight, Molecular Weight Distribution and Molecular Size of a Native Dextran, (1954).

Rosenfeld, E.L., et al., Clinica Chimica Acta, 10 223-228; Metabolism in Vivo of Clinical Dextran; Institute of Biological and Mediol Chemistry, Moscow (U.S.S.R.) (1964).

\* cited by examiner

COMPOSITIONS AND METHODS FOR INDUCING OR ENHANCING CONNECTIVE TISSUE REPAIR

CROSS-REFERENCE TO RELATED APPLICATIONS

This application is a U.S. national stage application under 35 U.S.C. §371 of PCT International Application Serial No. PCT/US2010/049640, which has an international filing date of Sep. 21, 2010, designates the United States of America, and claims the benefit of U.S. Provisional Patent Application Ser. No. 61/272,427, which was filed on Sep. 23, 2009. The disclosures of each of these prior applications are hereby expressly incorporated by reference in their entirety.

TECHNICAL FIELD

This invention relates generally to compositions and methods for treating and preventing excessive platelet activation in warm blooded subjects and pathophysiological sequelae therefore, including, but not limited to, using such compositions and methods to induce or enhance the repair of injured connective tissue.

BACKGROUND OF THE INVENTION

Repair techniques for partially ruptured, lacerated or severed tendons and ligaments (collectively denoted "cords") vary widely depending on the nature of the injury and the particular tendon/ligament affected. There are major differences in current treatment of injured cords, depending on the species of the subject (e.g., man, mammal, bird), the extent to which access can be obtained in the least obtrusive manner, in the amount of cord excursion, the surrounding environment, the stresses to which different cords are normally subjected, and in the healing characteristics of different cords. In addition, often there is no consensus of the overall best way to repair a given cord. Examples of often injured cords having different accepted repair techniques are flexor tendons of the human hand, the anterior cruciate ligament (ACL) of the human knee and the superficial digital flexor (SDF) tendon in the horse.

For example, repair of a long flexor tendon that has been severed is typically achieved by suturing the severed tendon ends face-to-face. Historically, the joints across which the tendon acts were immobilized from three to eight weeks to protect the tendon while it healed, particularly as a freshly sutured tendon can withstand only a fraction of the tensile force to which a healthy tendon is subjected during normal use. Immobilizing the tendon, however, can result in scarring and adhesion formation along the length of the tendon, as well as can adversely affect the range of motion of the tendon, particularly in the case of flexor tendons.

More recently, it has been discovered that flexor tendons have an intrinsic capacity to heal and that limited motion will actually expedite healing. The affected joints are most often partially immobilized to prevent inadvertent application of excess force.

In the case of an anterior cruciate ligament (connecting the bottom of the femur and the top of the tibia) the stresses resulting from applied forces are much greater, particularly as there is less interaction with surrounding tissue and bone, the excursion of the cord is less, and the healing tendencies are vastly different. Despite numerous studies, there still is no universally accepted repair procedure, and prevailing procedures are difficult and intricate. The current "standard of care" remains the reconstruction of the ACL using a bone-tendon-bone autograft (i.e., harvested from the patient). However, there are multiple problems with bone-tendon-bone grafting. The intact ACL possesses important mechanoreceptive and proprioceptive capabilities. Graft reconstruction sacrifices these capabilities. Autografting involves considerable donor site morbidity. To avoid donor site morbidity, occasionally a cadaveric gall is used; however, this carries the risk of disease transmission.

In the case of partially ruptured tendons, or in surgical manipulation or reconstruction of inured tendons, a viscous solution of hyaluronan (a.k.a. hyaluronic acid (HA)) is sometimes used primarily as a lubricant within the tendon sheath. Although it functions as a moderately effective lubricant in this scenario, extensive trials in horses designed to demonstrate improved healing or a reduction in recovery time have failed to show any benefit of intralesional HA (or PSGAG, another GAG, or B-aminoproprionitrile fumarate (BAPN), all three commonly prescribed for equine lameness) over controlled exercise alone (see Dyson S, 1977 & 2004).

In previous works, and as is described in U.S. Pat. No. 5,358,973), the present inventors have shown that a combination of HA and dextran also functions as an effective lubricant, preventing formation of adhesions between apposing injured surfaces, as may often occur in injured tendons between the tendon and the sheath within, which it normally freely glides.

Regarding the occurrence of non-elastic scarring after regeneration of injured connective tissue, it is well known that healing of skin and other connective tissues is often complicated by the formation of disorganized and unsightly scar tissue, as for example in wounds related to, but not limited to, burns, incisions and ulcers. Apart from the problems of scarring in tendons and ligaments referred to above, and to the obvious aesthetic and functional complications of topical (skin) and internal scar formation following most forms of invasive surgery, and in plastic surgery (e.g. breast augmentation) in particular, the compositions disclosed can also be applied to prevent scar complications in other tissues, including, but not limited to, prevention of blindness after scarring due to eye injury, facilitation of neuronal reconnections in the central and peripheral nervous system by elimination of glial scarring, and restitution of normal gut and reproductive functionality preventing strictures and adhesions after injury incurring in the gastrointestinal and reproductive systems.

In the indications described above and in connective tissue repair in general, platelets play a common pivotal and very early role in regulating connective tissue repair. This is achieved partly by rapid early release (degranulation) of arrays of cell signaling substances (cytokines) which initiate defensive cascade reactions and partly by their ability to pull together (retract) the meshwork of fibrin fibres which form most of the hemostatic plug when blood coagulates. Platelets thus regulate fibrin clot retraction, density and porosity, which partially determine the rate at which stem cells, fibroblasts and other cells involved in the wound healing process subsequently invade the hemostatic clot (see, S. Neuss, 2010).

Indeed, platelets have long been known to play a central role in the early initiation of events leading to blood clotting (hemostasis) and the inflammatory response. During evolution, when life-threatening grossly infected dirty traumatic wounds, often with major blood loss, were common events, platelets and leukocytes played a key role in survival, functioning as a rapid early warning defense system whereby activated platelets contributed to non-adaptive immunity and inflammation by rapidly secreting chemokines and cytokines that attract leukocytes to sites of crude injury and potential sepsis.

In modern times, when surgical procedures are performed with sterile instruments in a low bioburden environment, such cascades tend to overshoot their defensive role and utility, and constitute a pathophysiological risk to the patient instead, precipitating complications such as excessive inflammation, post-operative thrombosis, macro- and micro-embolism, excess thickening of the blood vessel wall (hyperplasia) and subsequent restenosis or occlusion, catheter occlusion and shedding of harmful platelet-leukocyte microemboli, which in their turn may trigger transient ischemic attacks (TIAs), stroke or myocardial infarction or may occlude or compromise the microcirculation in, for example, transposed skin or muscle flaps during reconstructive/plastic surgery.

The formation of platelet aggregates on the surface of atheromatous plaques and subsequent organization of these white thrombi into fibrous occlusive intimal lesions is undoubtedly one mechanism by which atherosclerotic lesions progress to severe obstruction and total occlusion; coronary artery thrombosis leading to myocardial infarction almost always occurs at the site of an atheromatous plaque. Percutaneous transluminal coronary angioplasty (PTCA) has become an important procedure to re-establish blood flow to the heart through partially occluded blood vessels. Unfortunately, approximately 30% to 40% of patients that have coronary angioplasty suffer restenosis of the treated vessel within 6 months of treatment; currently, there is no reliable method of preventing vascular restenosis. A revascularization procedure such as bypass surgery or another PTCA procedure is thus often required.

These complications are particularly devastating in most forms of vascular surgery but also present a challenge in less invasive vascular procedures such as PCTA (balloon angioplasty) and in various medical conditions characterized by impaired blood supply such as, but not limited to, acute stroke, acute pancreatitis, frostbite/gangrene, loss of hearing, etc. Activated platelets are not only involved in the etiology of these conditions but are also instrumental via their interaction with leukocytes in triggering "ischemia-reperfusion injury," which typically occurs when oxygenated blood flow is restored to an ischemic vascular bed after removal of a clamp, embolus or other obstruction to flow as, for example in organ or tissue transplantation, lysis of an occluding clot or on restoration of blood volume after hemorrhagic shock. This downstream "reperfusion injury" is generally mediated by free radical release from leukocytes which in their turn have been activated by cytokine release from activated platelets (see, Salter 2001).

Thus, interactions between activated platelets on the one hand and the endothelium, leukocytes, other cells, surfaces and fibrin in clot retraction, etc, on the other hand largely initiate and define the fate of the body's early defense against injury and sepsis. Platelet activation/degranulation following tissue injury is generally the trigger which activates leukocyte rolling and sticking to the vascular endothelium and in some injury scenarios may precede leukocyte recruitment and mobilization by as much as 3-5 hours, as for example in endotoxemic injury to the hepatic microcirculation (see, Croner, 2006). In other situations, however, this time lag may only be minutes or seconds.

Thus, events which are largely triggered by platelet activation, such as leukocyte activation, rolling and sticking to the endothelium of the microvasculature following ischemia-reperfusion (I/R) injury, may be used as surrogate indicators of underlying platelet activation.

We therefore speculate that the surprising synergistic effects of combining polysaccharides and HA which we disclose below may have a multifactorial etiology involving several interrelated synergistic factors including suppression of platelet activation, the presence of hyaluronan, and polymer-induced changes in the morphology, fragility and lysability of the fibrin clot thrilled in response to the acute injury.

In many of the surgical and medical scenarios described above, polysaccharides like dextran and, to some extent, HES, (and more recently GAGs like HA, such as discussed in U.S. Pat. No. 5,585,361) have long been used to suppress platelet hyperactivation and its inflammatory complications but often the doses required to attain effective and sustained protection are above the safe recommended doses of these agents.

For example, the risks of significant bleeding or renal complications with both dextran and HES are directly dose-related, and in situations where heparin or other anticoagulants are given at the same time, the doses of dextran or HES must be further reduced or omitted to minimize the risk of bleeding.

Both dextran and HES are also effective blood volume expanders. In some treatment scenarios, such as in stroke or threatening gangrene where the patient has not suffered significant blood loss, volume expansion may often be undesirable or contraindicated.

A synergistic interaction between dextran or other polysaccharides and HA thus offers an important therapeutic advantage in that the desired effect can be achieved by much lower and safer doses of each of the components.

An effective synergistic combination of HA together with dextran or HES, or both, therefore permits a reduction in total dextran or HES dosage without loss of the beneficial suppression of excess platelet activation, thus radically improving patient safety and offering the physician greater flexibility in devising optimal dosage regimes.

The present invention is intended to improve upon and resolve some of these known deficiencies within the relevant art discussed above.

SUMMARY OF THE INVENTION

The present invention provides compositions and methods for attenuating excessive platelet activation and subsequent pathophysiological sequelae or complications after tissue injury, including complications such as thrombogenesis, microembolism, restenosis, ischemia-reperfusion injury, inflammation and scarring. The compositions and methods are particularly useful for inducing or enhancing connective tissue repair without undue formation of fibrosis and non-elastic scar tissue. In accordance with certain aspects of the present invention, the compositions comprise a synergistic combination of biocompatible polymers in aqueous solution wherein the combinations comprise a glycosaminoglycan (GAG) together with a neutral polysaccharide.

In accordance with certain embodiments of the present invention, a composition capable of attenuating platelet hyperactivation comprising an aqueous solution containing from about 0.1% to about 7.0% by weight of a glycosaminoglycan and from about 1.0% to about 32% by weight of a neutral polysaccharide is provided. The glycosaminoglycan is selected from at least one of hyaluronan, chondroitin, dermatin, keratin, heparan, heparin, and GAG analogues dextran sulphate, pentosan sulphate, while the neutral polysaccharide is selected from at least one of an isomaltose oligomer, dextran, a hydroxyethyl starch, polyethylene glycol (PEG) and fucoidan.

In accordance with still other embodiments, the glycosaminoglycan component can be hyaluronan and the neutral polysaccharide component can be dextran. In accordance with this embodiment, the hyaluronan has a weight average molecular weight from about 1.5 kD to about 6,000 kD, while the dextran has a weight average molecular weight from about 0.3 kD to about 110 kD. In more specific embodiments, the hyaluronan has a weight average molecular weight of from about 2.5 kD to about 2,500 kD, while the dextran has a weight average molecular weight of from about 0.5 kD to about 50 kD.

In certain aspects of the present invention, the neutral polysaccharide of the composition capable of attenuating platelet hyperactivation can be a hydroxyethyl starch having a weight average molecular weight of from about 10 kD to about 500 kD, while in other embodiments the weight average molecular weight of from about 20 kD to about 350 kD. In accordance with still other aspects of the present invention, the neutral polysaccharide is an oligomer of isomaltose and has a weight average molecular weight of from about 0.3 kD to about 10 kD, more specifically from about 0.5 kD to about 4 kD.

In one form hereof, the glycosaminoglycan of the inventive composition capable of attenuating platelet hyperactivation is a partially cross-linked hyaluronan having a degree of cross-linking that is less than about 25%.

In still other embodiments, the composition capable of attenuating platelet hyperactivation further comprises at least one of an antioxidant, a scavenger, a cytokine, a growth factor, an interleukin, a gene therapy agent, a viscoelastic agent and a stem cell.

According to still another embodiment of the present invention, a method for treating platelet hyperactivation and associated diseases, conditions or pathophysiological sequelae thereof is provided. In accordance with this embodiment, an effective amount of an aqueous solution containing a glycosaminoglycan and a neutral polysaccharide is administered to a subject.

In accordance with certain illustrative aspects of the present invention, the associated diseases, conditions or pathophysiological sequelae of the treated platelet hyperactivation condition include a disorder selected from the group consisting of thrombosis, a thrombotic complication of an atherosclerotic disease, a thrombotic complication of an intervention of an atherosclerotic disease, a thrombotic complication associated with surgical or mechanical damage, a mechanically-induced platelet activation, a shunt occlusion, thrombosis secondary to vascular damage and inflammation, an indication with a diffuse thrombotic or platelet consumption component, venous thrombosis, coronary arterial thrombosis, a pathological effect of atherosclerosis and arteriosclerosis, a platelet aggregation and clot formation in blood and blood products during storage, a chronic or acute state of hyperaggregability, a reocclusion of an artery or vein following fibrinolytic therapy, platelet adhesion associated with extracorporeal circulation, thrombotic complications associated with thrombolytic therapy, thrombotic complications associated with coronary and other angioplasty, thrombotic complications associated with coronary artery bypass procedures, and disorders, procedures or sequelae characterized by inflammatory cascades triggered by platelet degranulation, including a disorder selected from the group consisting of an intimal hyperplasia, artheroma and restenosis of arteries or veins, platelet-leukocyte-fibrin micro- and macro-embolism, stroke, myocardial infarction, raised leukocyte activation, aggregation, adhesion and free-radical injury in association with ischemia-reperfusion injury following clot thrombolysis, declamping, angioplasty, organ and tissue transplantation, tissue salvaging reconstructive surgery or restoration of blood volume, in hypovolemia, inflammatory joint disorders and the sequelae of excessive fibrin dot retraction including fibrosis and scarring in connective tissue.

In one form thereof, the step of administering to the subject an effective amount of the aqueous solution comprises at least one of topically applying the aqueous solution to the subject or injecting the aqueous solution into the subject. In certain embodiments, the subject being treated comprises a mammal, such as a warm-blooded animal, including a human.

In accordance with still yet another aspect of the present invention, a method for repairing, regenerating, treating, or inducing the repair of an injury, a defect or a condition of a connective tissue by administering to a subject of an aqueous solution containing from about 0.1% to about 7.0% by weight of a glycosaminoglycan and from about 1.0% to about 32% by weight of a neutral polysaccharide is provided.

In yet other aspects of the present invention, a method for repairing, regenerating, treating, or inducing the repair of an injury, a defect or a condition of a connective tissue by administering to a subject an aqueous solution containing from about 0.1% to about 7.0% by weight of a glycosaminoglycan, from about 1.0% to about 25% by weight of a neutral colloidal polysaccharide and from about 0.3% to about 35% by weight of a neutral sub-colloidal crystalloid polysaccharide is provided, in accordance with this exemplary embodiment, the glycosaminoglycan has a weight average molecular weight from about 2 kD to about 5,000 kD, the neutral colloidal polysaccharide has a weight average molecular weight of from about 20 kD to about 100 kD and the subcolloidal crystalloid polysaccharide has a weight average molecular weight of from about 0.4 kD to about 4 kD.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described.

All references mentioned hereunder are incorporated by reference in their entirety. Unless mentioned otherwise, the techniques employed or contemplated herein are standard methodologies well known to one of ordinary skill in the art and the materials, methods and examples are illustrative only and not intended to be limiting.

As used herein, the term "connective tissue" includes, but is not limited to, ligament tissue, tendon tissue, cartilage tissue, skin, cornea and scar tissue.

As used herein the term "ligament" is intended to refer to both the rope-like structures of white fibrous connective tissue, which attach anterior extremities of interacting bones, as well as the tissue defining a synovial capsule. In accordance with non-limiting and illustrative embodiments of the present invention, the ligament can be an anterior cruciate ligament, a posterior cruciate ligament, a tibial collateral ligament, a fibular collateral ligament, a transverse ligament, a posterior menisco-femoral ligament, a posterior superior tibiofibular ligament, or a lateral collateral ligament, which is a complex of three ligaments that helps support the lateral side of the ankle joint.

As used herein, the term "tendon" is intended to define the connective tissue structure, which joins muscle to bone for example, and includes, but is not limited to, the achilles tendon, which is a tendon formed by the union of two muscles, the gastrocnemius and the soleus, which join in the mid-calf area and are known as the gastroc-soleal complex or Latissimus Dorsi Tendon, the posterior tibial tendon, the patellar tendon, the plantar flexor muscle-tendon unit and the rotator cuff tendon.

As contemplated by this invention, the implant or transplant may be in the site of the injury, defect or condition or may be adjacent to such injury, defect or condition. The differentiation, repair, regeneration, or treatment can be monitored by periodic assessment of tendon/ligament-like tissue formation, or tendon or ligament growth and/or repair. The progress can be monitored by methods known in the art, for example, X-rays (CT), ultra-sound, MRI, arthroscopy and histomorphometric determinations.

The composition of the invention may comprise, in addition to a tendon/ligament-inducing protein such as BMP-12 or VL-1 (BMP-13), other therapeutically useful agents including, but not limited to, MP52, epidermal growth factor (EGF), fibroblast growth factor (FGF), platelet derived, growth factor (PDGF), transforming growth factors (TGF-α and TGF-β), fibroblast growth factor-4 (FGF-4), parathyroid hormone (PTH), leukemia inhibitory factor (LIF/HILDA/DIA), insulin-like growth factors (IGF-I and IGF-II), and platelet rich plasma (PRP) and mesenchymal or other stem or progenitor cells. In addition, it should be understood and appreciated herein that portions of these agents may also be used in compositions of the present invention and such compositions may be useful for treating defects of the embryonic joint where tendon, ligaments, and bone form simultaneously at contiguous anatomical locations, and may be useful for regenerating tissue at the site of tendon attachment to bone.

It is contemplated that the compositions of the present invention may also be used in wound healing, such as skin healing and related tissue repair to avoid unwanted fibrosis or scarring. The types of wounds include, but are not limited to, burns, incisions and ulcers.

The preparation and formulation of such pharmaceutically/physiologically acceptable compositions, having due regard to pH, isotonicity, stability and the like, is within the skill of the art, and methods of administration include topically, systemically, or locally as an injectable and/or implant or device.

When administered, the composition for use in accordance with the present invention is, of course, in a pyrogen-free, physiologically acceptable form. Further, the composition may desirably be injected in a viscous form for delivery to the site of tissue damage. Moreover, topical administration may be suitable for wound healing and tissue repair.

In addition, the compositions of the present invention may be used in conjunction with presently available treatments for tendon/ligament injuries, such as suture (e.g., vicryl sutures or surgical gut sutures) or tendon/ligament allograft or autograft, in order to enhance or accelerate the healing potential of the suture or graft. For example, the suture, allograft or autograft may be soaked in the compositions of the present invention prior to implantation. It may also be possible to incorporate interleukins or gene therapy via vectors into the composition of the invention or incorporate the composition onto suture materials, for example, by freeze-drying.

The compositions may be in a carrier such as an appropriate matrix and/or sequestering agent. For instance, the matrix may support the Composition or provide a surface for tendon/ligament-like tissue formation and/or other tissue formation. To this end, the choice of a carrier material may be based on biocompatibility, biodegradability, mechanical properties, cosmetic appearance and interface properties. The particular application of the compositions will define the appropriate formulation. Potential matrices for the compositions may be biodegradable and chemically defined. Biodegradable materials, such as cellulose films, or surgical meshes, may also serve as matrices. Such materials could be sutured into an injury site, or wrapped around the tendon/ligament.

Specific classes of carriers in accordance with the present invention may include polymeric matrices, such as polymers of poly(lactic acid), poly(glycolic acid) and copolymers of lactic acid and glycolic acid. These matrices may be in the form of a sponge, or in the form of porous particles, and may also include a sequestering agent.

Additional optional components useful in the practice of the subject application include, e.g., antimicrobial preservatives such as methyl and propyl parabens and benzyl alcohol; antioxidants such as EDTA, hydralazine, glutathione, citrate and BHT (butylated hydroxytoluene); antibiotics, surfactants such as poly(sorbates) and poly(oxyethylenes); and viscoelastic agents such as high or very high Mw HA to adjust viscosity, etc.

Advantageously, the compositions include further components, such as osteoinductive or osteoconductive materials, medicaments, stem or progenitor cells, and three-dimensional structural frameworks.

As will be explained in detail below, the present invention relates to the surprising discovery that the disclosed combinations of biocompatible polymers, comprising a glycosaminoglycan (GAG) together with one or more neutral polysaccharides, act synergistically to induce, enhance or accelerate the repair and organized regeneration of a connective tissue injury without the formation of undesirable fibrosis and non-elastic scar tissue.

In accordance with certain aspects herein, the inventive compositions and methods are predicated on the surprising finding that combinations of GAGs and neutral polysaccharides interact synergistically to suppress excessive activation of platelets following tissue injury, thus blocking or attenuating a wide range of inflammatory cascades involved in the etiology of many medical and surgical complications.

Given the crucial role of excessive platelet activation in the etiology of a wide range of pathophysiological processes and complications, including those described above, the regulation of excessive platelet activation by the compositions disclosed herein can be an invaluable tool in reducing the risk of undesirable or life-threatening complications of surgical or medical treatments.

The synergistic suppression of excessive platelet activation by the presently disclosed combination of polymers naturally affects many other physiological processes and cascades in which platelet activation plays a key role. One well documented example is the formation and retraction of a blood clot or thrombus, which involves a complex cascade of events mediated by an array of signal substances released primarily by platelets entrapped in the fibrin fiber network of the clot or thrombus. Clot stabilization and retraction in particular is mediated by activated platelets which link and pull the component fibrin fibers closer together, increasing clot density and reducing porosity (see, Carr & Carr, 1995).

Naturally, any suppression of platelet function in this respect will impact these processes, reducing retraction forces binding the fibrin meshwork together, reducing clot density and increasing its porosity and penetrability to invading mesenchymal stem cells (MSCs) and fibroblasts both of which secrete fibrinolytic enzymes to better enable them to penetrate the fibrin clot. Not surprisingly, the ease and rate at which these progenitor cells penetrate the clot are significant factors in accelerating orderly regeneration of collagen fibrils (see Neuss, S., 2010).

At the same time, polymerization of fibrin to form the fiber network of the clot is radically modified by the presence of the colloids in the composition, in that the fibers formed are much thicker yet also less dense and more easily lysed by MSCs and the body's own enzymes.

This additional effect on fibrin mesh morphology and porosity permits a more rapid lysis and elimination of the initial disorganized clot or thrombus, paving the way for the earlier influx of fibroblasts and other cells involved in organized repair. The present findings surprisingly indicate that this latter aspect may be particularly important in the repair of ruptured tendons or ligaments where it is important that fibrin clots formed at the lesion (tear or injury) by leakage of blood or lymph from torn capillaries do not form persistent disorganized non-elastic scar tissue, but are lysed endogenously at an early stage so as to create space and an organized environment for the neogenesis of primarily coaxially aligned collagen fibrils for maximum elasticity.

Both glycosaminoglycans (GAGs) and polysaccharides (such as dextrans or HES) are polymers containing mixtures of differently sized molecules, each composed of basic repeating units, which, for polysaccharides are glucose, and for GAGs like HA are disaccharides composed of D-glucuronic acid and D-N-acetyl-glucosamine.

Because polymers are polydisperse, they have no exact molecular weight but must be defined by weight average (Mw) or number average (Mn) molecular weights, or more precisely by a molecular weight distribution curve. As used herein, the terms Mw and Mn are intended to imply the meanings as defined above. In addition, the use of the term "dextran 60," for example, or "HES 130," etc., shall mean a dextran with a Mw of ca 60,000 Daltons (or 60 kD) just as "HES 130" shall mean HES with a Mw of ca 130,000 Daltons (or 130 kD).

These polymers are also "polydisperse." For example, ca 80% of the molecules in clinical grade dextran 60 (i.e. Mw=60 kD or 60,000 Daltons (Da)), referred to in Example 1 below, will generally lie between 14 kD and 115 kD but dextran 60 also contains significant portions (>5%) of small dextrans in the ranges 0.5 kD-10 kD at the low end, and a similar proportion of very large molecules exceeding 200 kD.

The GAG components of the invention may include, but are not limited to, natural proteoglycans, and the glycosaminoglycan moieties of proteoglycans. GAGs may be sulphated like chondroitin, dermatin, keratin or heparan, or may be unsulphated like hyaluronan (HA) or heparin. Alternatively, analogues of glycosaminoglycan, like dextran sulfate or pentosan sulphate may be used. In accordance with yet still other embodiments herein, hyaluronan (HA) may be used. Some so-called "cross-linked" GAGs, such as cross-linked HA (e.g. Synvisc (Genzyme), contain a relatively low content of cross-linked material. In such cases, where most of the molecules exist as free unbound HA, the preparation is regarded as HA for the purposes of this invention.

Hyaluronan is rapidly broken down in the circulation by at least two forms of hyaluronidase. Thus, the intravascular (plasma) half-life of a high molecular weight HA, (e.g., having a Mw of 2,000 kD) is relatively short, generally less than one hour, depending upon the total dose given. At the cellular level, HA is degraded progressively by a series of enzymatic reactions that generate polymers of decreasing sizes, the various small fractions often triggering different signal transduction pathways.

Thus a high molecular weight HA can be administered by parenteral injection and function as a pro-drug for in-vivo generation of smaller fractions like the HA fractions used in Example 1. In Example 1 below on the effects of HA and polysaccharides on platelet activation, the effects of several sharp HA fractions with molecular weights (Mw) between of 1.53 kD and 250 kD were investigated. Although all the fractions within this range significantly reduced platelet activation, the effects were most pronounced at a Mw of about 2.67 kD.

In contrast to HA, dextrans are not normally degraded in plasma but are only broken down by the liver or the reticuloendothelial system (RES). The intravascular (plasma) half-lives of dextrans are therefore much longer than for HA—ranging from ca 30 minutes for small fragments of dextran of Mw ca 1 kD to over 10 hours for dextran 70 kD, partly depending on renal function since molecules smaller than ca 20 kD are freely excreted via the kidneys (see, Arfors, Buckley, 1997). The plasma half-life of HES depends on Mw but is also much longer than for HA.

It should be noted, however, that the half-lives of both HA and polysaccharides can be much longer when administered into tissues with relatively poor blood supply, such as connective tissue (e.g. cartilage, tendon, ligament, cornea, etc), or into avascular compartments, like the synovial (joint) space.

It is therefore possible for those skilled in the art to adjust the doses and relative proportions and molecular weights of each component in the polymer combinations disclosed to "tailor make" formulations for optimal duration of effect in each specific application and tissue, and for each specific type and extent of injury.

One specific polysaccharide component of the disclosed compositions is clinical dextran, which like other polymers, occurs as a mixture of different size molecules ranging in size from isomaltose oligomers with Mw of ca 0.3 kD to macromolecules with Mw well over 100 kD. Dextran fractions within this wide range of molecular weights are well documented to suppress excessive platelet activation and its subsequent pathophysiological sequelae, including leukocyte activation, thrombogenesis, etc. (see, Arfors, Buckley, 1997).

As indicated above, the molecular weight of the dextran fraction used will determine its plasma or tissue half-life, particularly if most of the fraction lies below the renal threshold for dextran, which is approximately 20 kD. Thus, very small molecules of dextran (e.g., oligomers of isomaltose) are rapidly removed from the circulation. However, when different dextran fractions are studied at equivalent or fixed plasma concentrations, their effects on platelets and downstream cascades appear to be essentially similar, at least for dextran fractions within the accepted "clinical" Mw range (ca 0.5 kD to about 101 kD).

Steinbauer et al., 1997 & 1998, for example, found no significant difference between the effects of dextran fractions with Mw values of 1 kD, 40 kD, 60 kD, 70 kD, 110 kD and 150 kD on a surrogate marker of platelet activation, leukocyte adherence, in a standard hamster ischemia-reperfusion injury model 30 minutes after reperfusion. As expected, however, measurements at later time points after reperfusion, reflected the shorter plasma half-lives of the smaller dextran fractions in particular. Thus, in Example 1 below, a representative broad fraction of dextran 60 in which 80% of molecules lie between ca 14 kD and 180 kD and >5% lay below ca 10 kD was chosen to represent the clinical dextran Mw range from 1 kD to 110 kD with regard to dextran's specific effects on the activation and degranulation of platelets and subsequent leukocyte adherence 30 minutes after reperfusion.

The polysaccharide component of the invention, to be used in combination with one or more of the GAGS above, may consists of one or more fractions of a clinically acceptable neutral polysaccharide, such as a dextran, or a substituted starch such as hydroxyethyl starch (HES) or biocompatible fractions of polyethylene glycol (PEG) or fucoidan.

The polysaccharide component may be a small sub-colloidal fraction (Mw<15 kD) such as isomaltose oligomers (i.e hydrolysed dextran) mannitol. Alternatively, it may be a higher molecular weight colloidal fraction where most of the polysaccharide molecules lie above the renal and capillary thresholds (>20 kD), such as Dextran 40 or 60 or HES 130 or 200. The polysaccharide component may alternatively be a pharmaceutically acceptable mixture of both sub-colloidal and colloidal polysaccharides.

In accordance with certain aspects of the disclosed composition, the colloidal polysaccharide is a dextran with Mw of about 0.3 kD to about 100 kD. In another embodiment, the polysaccharide component is a sub-colloidal polysaccharide, including isomaltose oligosaccharides with weight average molecular weight (Mw) of about 0.3 kD to about 10 kD. In yet another aspect of the present invention, the polysaccharide component is a bimodal mixture of both a sub-colloid fraction of dextran (a.k.a., isomaltose oligomers) and a colloidal fraction of dextran.

The sequelae or complications which the disclosed composition may be used to prevent or treat include, but are not limited to, any pathophysiological or undesirable consequence, direct or indirect, of excessive platelet activation, including but not limited to thrombogenesis, formation of macro- and micro-emboli, leukocyte hyperactivation, atheroma or hyperplasia formation and restenosis, ischemia-reperfusion injury, and excessive fibrin clot retraction, including suboptimal healing of connective tissue injuries, resulting in non-elastic scarring or fibrosis formation in cords, skin or cornea.

In one aspect of the present invention, a method of treatment or prophylaxis of a traumatic or ischemic condition in a warm blooded subject (e.g., a human) is provided. In accordance with this aspect of the present invention, the method comprises administering to a subject a therapeutic composition containing hyaluronic acid (HA) and a neutral polysaccharide in a dosage effective to inhibit excessive activation, adherence and aggregation of platelets within the subject's vascular system. In certain, aspects, the traumatic or ischemic condition is a traumatic accident, such as blunt or penetrating injury and may involve major blood loss, a fracture, a ruptured tendon or ligament, an intentional trauma, such as a surgical operation, particularly major prolonged surgery, blood loss or a vascular occlusion, which can lead to the development of pulmonary emboli (e.g., iliofemoral thrombosis, mesenteric vein thrombosis and Budd-Chiari syndrome).

In one form herein the present invention is particularly useful for treating or preventing thrombosis or microemboli in patients who have not sustained major blood loss and therefore may not tolerate large doses of dextran or other volume expanders as, for example, in hemorrhagic stroke. In another form herein, the ischemic condition is arterial thrombosis, particularly coronary artery thrombosis, where further platelet activation may be deleterious.

In accordance with yet other aspects of the present invention, a method of preventing or reducing thrombogenesis or the formation of microemboli in a warm blooded subject at risk of developing such complications is provided, in accordance with this aspect of the present invention, a subject is administered a therapeutic composition containing hyaluronic acid plus polysaccharide at a dosage effective to inhibit the adherence and aggregation of platelets. In accordance with one exemplary embodiment of this aspect of the invention, the subject may have an increased risk of developing a thrombus due to a medical condition which disrupts hemostasis, including heparin induced thrombocytopenia, coronary artery disease, atherosclerosis, pregnancy, stroke, neoplasia, obesity, systemic lupus erythematosus, nephrotic syndrome, polycythemia vera, inflammatory bowel disease, homocystinuria, hyperhomocysteinemia, paroxysmal nocturnal hemoglobinuria, shock and congestive heart failure. In further aspects, the mammal may have an increased risk of developing a thrombus or microemboli due to a medical procedure, including cardiac surgery, cardiopulmonary bypass, catheterization, percutaneous transluminal coronary angioplasty and atherotomy, as well as procedures which involve the placement of either a synthetic or bioprosthetic prosthesis (e.g., a cardiovascular valve).

It should be understood and appreciated herein that in accordance with certain of the disclosed aspects of the present invention, the combination HA and polysaccharide may be administered systemically or locally. Moreover, the administration of HA and polysaccharide may occur prior to, during, or after a medical or surgical procedure, or treatment with other agents (e.g., thrombolytic agents).

In still another aspect of the present invention, a method of inhibiting the adherence of platelets to the surface of a prosthetic device by coating the device with hyaluronic acid plus polysaccharides in an amount sufficient to inhibit the interaction of the platelets with the surface of the device prior to exposure of the device to the platelets is provided. In accordance with this aspect of the invention, the device can be made of any suitable biocompatible material, either totally or partially synthetic, that is commonly used in medical procedures. In certain embodiments, the prosthetic device is a coronary valve, vascular graft or a stent.

In still another aspect of the present invention, a method for inducing or enhancing the repair and regeneration of injured connective tissue or skin without undesirable formation of non-elastic scar tissue is provided. In accordance with this embodiment, the disclosed composition is placed into contact with the injured connective tissue, such as a tendon or ligament, skin or cornea.

In accordance with certain embodiments, the invention also provides methods of treating intra- and extra-articular injuries in a subject (e.g., a mammal) by contacting the ends of a ruptured tissue from the subject with the compositions of the invention. In accordance with this aspect of the present invention, intra-articular injuries include, for example, meniscal and ligament tears, while extra-articular injuries include, for example, injuries to the ligament, tendon or muscle.

In accordance with certain aspects of the present invention, a method of treating the acute inflammation of a joint as, for example, after trauma or acute overloading as in (sports) injury related knee osteoarthritis is provided by introducing the disclosed compositions into the joint. It should be understood and appreciated herein that the inventive methods and compositions may also be similarly used for treating chronic inflammatory states such as rheumatoid arthritic joint disorders where cytokine release from activated platelets has recently been reported to play a key role in the generation of inflammation (see, Boilard, 2010).

In this context it may be noted that injection of dextran alone (either mono- or bi-modal fractions) into inflamed joints has been shown to reduce inflammation and pain as reported by one of the present inventors in U.S. Pat. No. 5,902,800. While it is known by those of ordinary skill in the art that endogenous high molecular weight HA is present in the joint synovial fluid and that the adjustment of viscosity or lubricating properties of the dextran solution may be made by addition of viscoelastic agents (which could include HA), the present inventors are unaware of any teaching or suggestion of a specific synergistic interaction between dextral and HA in terms of (or in regard to) their presently disclosed effects on platelet activation and its associated sequelae, including inflammation, or on their novel synergistic effects on the regeneration of injured connective tissue.

In light of the novel synergistic effects of dextran and HA as disclosed herein, a skilled artisan would be able to devise more informed and flexible dosage strategies for inflammatory joint disease, particularly where excess polysaccharide-induced volume expansion of the synovial joint is undesirable or contraindicated. In this respect, the combination of HA with high concentrations of very small molecules of dextran or isomaltose oligomers (Mw 0.3 kD-10 kD) will reduce excess volume expansion and side effects associated with high Mw dextrans, yet still meet the conditions for synergy with HA, as disclosed below.

Furthermore, the findings disclosed in Example 1 below, indicate that synergy between dextran and HA is optimal when HA has a low Mw 250 kD). Since enzymatic degradation of high Mw HA occurs in circulating blood, intravascular administration of high Mw HA (e.g. Mw 2,000 kD) into the blood stream will function as a pro-drug for delivery of lower Mw HA moieties to the inflamed tissue.

In avascular compartments, however, like the synovial. (joint) space, this rapid degradation does not occur. Since the synovial apace normally contains endogenous HA with very high Mw (>3,000 kD), and there is little access to circulating hyaluronidase, the rate of degradation (and generation of HA moieties <250 kD) is substantially slower than in blood. Thus, the injection of dextran alone into the joint (i.e. its in-vivo admixture with very high Mw endogenous HA) will not create optimal conditions for promoting synergistic interaction between dextran and HA since the Mw of the synovial HA is too high.

Although the Mw of endogenous synovial HA is often lower in severe inflammatory flare-ups of the joint, it seldom falls below 2,000 kD, still far higher than the optimal HA Mw range (<250 kD) for synergy with dextran or other polysaccharide. As such, in accordance with certain aspects of the present invention, a method of treating an inflammatory joint disorder in warm-blooded animals (including humans) can comprise intra-articular injection of a co-mixture of a biocompatible neutral polysaccharide, such as dextran, oligomers of isomaltose, HES, PEG or fucoidan and HA, which can have a Mw below 2,000 kD, or more specifically below 500 kD in accordance with this aspect of the present invention, the Mw of the dextran may lie, between about 0.3 kD and about 110 kD.

It should be understood and appreciated herein, however, that the presently disclosed methods do not exclude the addition of a suitable amount of high or very high molecular weight HA (linear or cross-linked) or other viscoelastic agents solely for the purpose of adjusting viscosity or lubrication as mentioned in U.S. Pat. No. 5,902,800.

In certain specific aspects of the present invention, the HA component of the disclosed composition when used for systemic administration in the blood to prevent platelet activation or adhesion and their pathophysiological sequelae, is given in the range of about 3 mg/kg body weight to about 600 mg/kg, wherein the polysaccharide component of the composition for the same purpose is given in the range of about 3 mg/kg to about 2000 mg/kg.

The viscosity of the disclosed composition of HA and polysaccharide as a solution should be less than 1000 centipoise and greater than 15 centipoise. The molecular weights of both HA and polysaccharide components can be adjusted according to the desired viscosity for a specific concentration of HA and polysaccharide.

In accordance with certain embodiments, the average molecular weight of the HA is greater than about 1.5 kD; more specifically, between about 2.6 kD and about 3,000 kD and even more specifically, between about 100 k and about 2,000 kD. En still other embodiments, the average molecular weight of the polysaccharide is between about 0.3 kD and 110 kD, more specifically between about 0.5 kD and about 70 kD, and even more specifically, the polysaccharide has a bimodal molecular weight distribution obtained by mixing a very low molecular weight polysaccharide with Mw range from about 500 D to about 10 kD together with a higher molecular weight polysaccharide with a Mw range from about 20 kD to about 75 kD.

For the local administration of HA and polysaccharide solution at the site of intended action to prevent excessive platelet activation or clot retraction, the concentration of the HA component lies between about 0.1% and about 7% and the polysaccharide component lies between about 1% and about 32% and the viscosity of the combination of HA plus polysaccharide lies in the range of about 20 centipoise to about 300,000 centipoise.

In accordance with certain embodiments of the present invention, the composition is an aqueous solution of biopolymers containing hyaluronan in an amount of about 0.1% to about 7% (w/v), and dextran or HES, in an amount of about 1 to about 25% (w/v), the hyaluronan having a weight average molecular weight (Mw) within the range of about 1.5 kD to about 6,000 kD, dextran having a Mw within the range of about 0.3 kD to about 110 kD and HES having a Mw within the range of about 10 kD to about 500 kD.

In accordance with still other embodiments of the present invention, methods of implanting or injecting the polymer combination described above into an injury, defect or condition of the tissue in need of such treatment are provided, while in accordance with yet other embodiments, the compositions are useful for regenerating connective tissue, and can be administered to an area having injury to, or a loss of, connective tissue, such as bone, cartilage, tendon, and ligament.

Advantages and improvements of the processes, methods and compositions of the present invention are demonstrated in the following examples. These examples are illustrative only and are not intended to limit or preclude other embodiments of the present invention.

EXAMPLE 1

The effects of various sharp fractions of hyaluronan (HA) and dextran on platelet rolling and sticking in the microcirculation were investigated in viva in a standardized mouse small intestine model by intravital fluorescence microscopy using platelets labeled ex-vivo with rhodamine-6G infused i.v. during reperfusion.

Under anesthesia, female Balb/c mice were subjected to midline laparotomy and a jejunal segment was gently exteriorized; 90 minutes of intestinal ischemia were induced by occlusion of the segmental artery by microclip, followed by reperfusion for 30 minutes to simulate ischemia-reperfusion injury (I/R). This standard injury induced a highly significant increase in platelet rolling and adhesion to the endothelium of arterioles and venules compared with sham controls.

Additional groups of animals were given low intravenous (iv) doses (10-30 mg/kg) of several different sharp (monomeric) fractions of pure pyrogen-free HA, from a Mw of 1,530 D to a Mw of ca 250,000 D. All groups consisted of 5 or 6 animals, values recorded as mean+/−SEM. At both the 30 mg/kg and 10 mg/kg dose levels, all fractions of HA significantly reduced the effects of I/R injury on platelet rolling and adhesion in arterioles ($p<0.05$ vs. I/R).

The following results were obtained when effects of the lowest HA dose (10 mg/kg) on platelet activation were compared with very low doses of dextran 60 (5 mg/kg) and with combinations of these same polymers at the same doses in the same model.

In arterioles, firm adherence of platelets was reduced from a mean of 805 mm-2 in the group subjected to I/R alone, to a mean of 410 mm-2 in those subjected to I/R followed by HA (10 mg/kg). Mean value for platelet adherence in those receiving 5 mg/kg dextran 60 alone after I/R was ca 190 mm-2. The corresponding mean value for the group receiving a combination of 10 mg/kg HA and 5 mg/kg. Dextran 60 after I/R was 130 mm-2 ($p<0.05$ vs. I/R).

Rolling of platelets in arterioles responded to I/R, HA and Dextran 60 in a similar manner; I/R induced a sharp increase in platelet rolling from 2 mm-1 per sec/mm (sham) to 30 mm-1/s/mm, whilst 10 mg/kg HA after I/R reduced rolling to 24 mm-1/s/mm. Dextran 60 alone (at 5 mg/kg) reduced rolling after I/R to ca 21 mm-1/s/mm whilst the combination of 10 mg/kg HA+5 mg/kg Dextran 60 reduced rolling after I/R to 6 mm-1/s/mm. ($p<0.05$ vs. I/R).

Despite the striking anti-adhesion effects above of both HA and dextran in arterioles, on the venular side, platelet adhesion was not significant reduced by either 10 mg/kg HA or by 5 mg Dextran 60.

Platelet rolling in venules, however, was significantly reduced by both HA alone and dextran alone and to a far greater extent by the combination of 10 mg/kg HA+5 mg/kg Dextran (the corresponding values for sham, I/R, 10 mg/kg HA, 5 mg/kg Dextran and the HA/Dextran combination being: 3, 34, 20, 15, and 10 mm-1/s/mm, respectively).

Thus, at the time point chosen (30 min after reperfusion) both HA and dextran injected separately in very low doses significantly reduced the intense platelet activation and adherence induced by 90 minutes of ischemia.

The combination of a very low dose (5 mg/kg) of dextran (i.e. at a dose far too low to exert any volume expansion, hemodilution or other rheological effects on the circulation) given together (simultaneously) with HA reversed the effects of IRI on platelets to a much greater effect than HA or dextran given separately and alone; thus, exhibiting a pronounced synergistic effect.

As noted above, all dextran fractions within the "clinical" molecular weight range (1 kD to 110 kD) exhibit similar well documented suppression of platelet hyperactivity and of downstream platelet-induced cascades such as those involved with leukocyte activation and recruitment, at equivalent intravascular concentrations. For this reason, a relatively broad fraction of dextran 60 in which ca 80% of the mol mass distribution lies between 14 kD and 180 kD with significant fractions (>5%) in the ranges 0.5 kD-10 kD and 190 kD-210 kD was used as a representative dextran in the above Example 1.

Although the intravascular half-life of HA is much shorter than that of dextran, it should suffice to synergistically reinforce the effects of dextran in attenuating excessive platelet activation and degranulation in the crucial early phase after trauma when inflammatory cascades are initially triggered. Suppression of this early phase in cascade generation is important if subsequent downstream complications of excess platelet activation are to be prevented.

Therefore a judicial combination of i.v. HA and dextran not only ensures maximum control of excess platelet hyperactivity right at the crucial early phase of platelet activation immediately following trauma, but also permits sustained control over a longer period of up to 8-10 hours (e.g. overnight after surgery) to ensure optimal prevention of complications. In this respect, use of HA alone to suppress hyperactivated platelets is not an option in many treatment scenarios.

EXAMPLE 2

By way of background, tendons and ligaments are the leading cause of "down time" in equine related industries. Injury to the superficial digital flexor tendon (SDFT) in particular is a career limiting injury with a high incidence of reinjury (see, Dyson S, 2004). These injuries consume valuable time and resources with the plethora of new generally ineffective treatment options now being offered. Although some limited advances have been claimed, as for example with autologous stem cells, down time (unproductive convalescent time) is still in excess of 12 months (see, Stashak, 2002, p. 617).

Previous studies employing intralesional hyaluronan (HA) (Dyson S, 1977, 2004) concluded "there appears to be no benefit of treatment with either hyaluronan or PSGAG compared with controlled exercise alone."

A study was therefore set up to investigate whether previously poor historical results in treating SDF tendon injuries with intralesional 1% hyaluronan (HA) alone could be improved upon by the intralesional injection of a combination of hyaluronan with a mixture of colloidal and sub-colloidal polysaccharides (coded GLV11, consisting of 1% HA (Mw ca 1,500 kD), 10% dextran 70 and 1.2% isomaltose oligosaccharides as described in the current invention).

The combination of HA and dextran was injected directly into the lesion in the core of the tendon, not into the sheath or adjacent tissues, in order to clearly differentiate between its physical lubricant properties and its now disclosed surprising ability to accelerate regeneration of injured connective tissue in the core of the tendon.

To date, 246 horses with ultrasonic evidence of acute tendon or suspensory ligament injuries have been entered into the study. The subject population includes all major breeds, sex, age and performance levels 54% Standardbreds, 12% Quarterhorses, 8% Thoroughbreds, 8% barrel horses, 13% hunters and 4% others.

Ages ranged from 3 years to 17 years of age with a mean age of 7.12 and a median age of 7.50% of the horses had suspensory lesions, 31% had superficial flexor tendon lesions and 13% had XYZ ligament or distal sesmoidian ligament damage. Lesions have ranged from 1%-80% of tendons and 5%-50% of suspensory ligament damage. Of these horses, 69% were geldings, 25% stallions and the rest mares.

Methods:

All horses received an ultrasound within 24 to 48 hours of injury. The areas of the injuries were surgically prepared and GLV11 was aseptically injected intra lesionally at a dosage of 1 cc per cubic cm of damaged tissue. A Gelocast was applied and changed after 48 hours. The second Gelocast was removed after an additional 48 hours.

When possible, horses were aquasized for the next 14 days. In the event water therapy was not available, the horse was hand walked twice per day for 40 min. After the 18th day, the horse was returned to light work for 14 days and then resumed training after a follow up ultrasound exam. Most of the horses were exercising 6 miles per day at the extended trot. The horses were then allowed to resume racing or showing according to the trainers decisions.

Results to Date:

Of the 246 acute tendon/suspensor (ligament) injuries treated to date, 94% have returned to competition in less than 50 days with 92% remaining sound for a minimum of 3 months or 12 races depending on breed.

This compares dramatically with the 12 months normally required to return a horse to racing despite treatment with HA alone. According to Dr. Sue Dyson, a leading international authority on equine tendon injuries, the incidence of recurrent tendon injury in horses treated with 1% HA alone ranged from about 20 to 57% in a study previously performed by her on a similar horse population (see, Dyson S., 2004). Other historical data on tendon injuries indicate that only 20-60% of these horses return to racing. Some 80% are reinjured in racing and 44% of show horses are also reinjured.

CONCLUSION

Considering the broad range of the horses ages, breeds and sex variations, the return time to performance levels, given varying injuries, was extremely short. This surprising reduction in "down-time," together with the very low rates of recurrent injury indicate that the combination of HA with isomaltose oligomers and colloidal dextrin not only accelerates tendon/ligament repair, but also restores the strength and elasticity of these tissues to their original pre-injury condition.

The results exhibited show quite objectively by sonographic imaging and early return to normal racing without undue reinjury rates that regeneration and sustained healing of the lesion occur in less than one quarter of the time normally required in horses treated conventionally by controlled exercise or with hyaluronan, PSGAG or BAPN alone. In this respect, the economic benefits of reducing performance "down time" for the equine industry are very significant. The same benefits in terms of reduced suffering and costs also apply to human connective tissue injuries, not least tendon and ligament injuries in sportsmen, or trauma patients.

The results of the equine studies show that not only is recovery time significantly reduced, but also reinjury rates, after resumption of racing, are surprisingly low, which indicates that the elasticity and strength of the new collagen fibrils regenerated in the lesion are well comparable with those in uninjured tendon i.e. that regeneration of most collagen fibrils has occurred in good coaxial alignment with the tension gradient. This is in contrast to the problem of disorganized non-elastic scarring and persistent suboptimal collagen neogenesis, which are reported to occur for at least 14 months after tendon injury when the lesion is left to heal without specific treatment (see, Williams, I F, 1985).

With regard to the prevention of non-elastic scar tissue following acute tendon or other connective tissue injury, the present inventors speculate that other factors or components of the disclosed composition may also theoretically contribute to the surprising synergy observed in the examples above between the key components of the disclosed composition.

It is well documented, for example, that hyaluronan (HA) is found in embryonic and fetal tissues in much higher concentrations than in corresponding tissues in adults. Since fetal wounds heal with minimal inflammatory response and without evident scarring, and this appears (see, in in-vitro work by Olutove, O O, 1997) to be related to the presence of HA, it is tempting to speculate that the HA component of the present inventive compositions may contribute to the surprising in-vivo results disclosed herein. Other authors, however, (see, Dyson, S, 1997 & 2004) have failed to show any significant improvement in tendon repair using HA alone in an extensive In-vivo trial on 219 horses.

It is also well documented that fibrin formed in the presence of neutral carbohydrate polymers such as dextran, hydroxyethyl starch (HES) or fucoidin, tends to form much thicker fibers during polymerization, and the resulting clot is more fragile and more easily lysed by the endogenous fibrinolytic enzyme iPA (see, Strauss 1985 Carr, 1995).

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fail within the limits of the appended claims.

REFERENCES

The following references are incorporated herein by reference in their entirety:

1. DYSON S. J., Treatment of superficial digital flexor tendonitis: a comparison of conservative management, sodium hyaluronan and glycosaminoglycan polysulphate, *Proc. Am. Ass. Equine Practnrs.* 43, 297-300, 1977;
2. DYSON S. J. Medical Management of Superficial Digital Flexor Tendonitis: A Comparative Study in 219 horses (1992-2000) *Equine Veterinary Journal* 2004: 36: 415-419;
3. WILLIAMS et al., Development of collagen fibril organization and collagen crimp patterns during tendon healing, *International Journal of Biological Macromolecules*. Vol 7, Issue 5, October 1985, Pages 275-282;
4. NEUSS S., et al., Secretion of fibrinolytic enzymes facilitates human mesenchymal stem cell invasion into fibrin clots. *Cells Tissues Organs,* 2010; 191(1):36-46;
5. SALTER J W, et al., Platelets modulate ischemia/reperfusion-induced leukocyte recruitment in the mesenteric circulation. *Am J Physiol Gastrointest Liver Physiol*. 2001 December; 281 (6):G1432-9;
6. CRONER R S, et al. Hepatic platelet and leukocyte adherence during endotoxemia. *Crit Care* 2006 February; 10 (1):R15;
7. OLUTOYE O O, et al. Hyaluronic acid inhibits fetal platelet function: implications in scarless healing, *J. Pediatr Surg.* 1997 July; 32 (7):1037-40;
8. STRAUSS R G, et al., Effects of hydroxyethyl starch on fibrinogen, fibrin clot formation, and fibrinolysis. *Transfusion*. Volume 25, Issue 3, pages 230-234, May-June 1985;
9. CARR, M. et al., Fibrin structure and concentration alter clot elastic modulus but do not alter platelet mediated force development, *Blood Coagulation & Fibrinolysis*. 6 (1):79, February 1995;

10. ARFORS K E, et al., Pharmacological characteristics of artificial colloids. (1997) Bailliere's Clinical Anaesthesiology, 11 (1), pp. 15-47;
11. STEINBAUER M, et al., Effects of dextran on microvascular ischemia-reperfusion injury in striated muscle. *Am. J. Physiol.* 272: H1710-H1716, 1997;
12. STEINBAUER M, et al., Impact of dextran on microvascular disturbances and tissue injury following ischemia/ reperfusion in striated muscle. *Shock*, 9, 5, 345-351, 1998;
13. STASHAK T S, (ed) *Adams' Lameness in Horses* 5th Edition, pages 612-617 Publisher: Lippincott, Williams & Wilkins (June 2002);
14, BOILARD E., et al., Platelets amplify inflammation in arthritis via collagen-dependent microparticle production. *Science,* 2010, Jan. 29: 327 (5965): 580-3.
15. Dowling B A, Dart A J, Hodgson Dr, et al. Superficial Digital Flexor Tendonitis in the Horse. *Equine Veterinary Journal* 2000; 32: 369-378;
16. Ross M W, Dyson S J, Superficial Digital Flexor Tendonitis, IN Ross M W, Dyson S J, eds Diagnosis and Management of Lameness in the Horse, St. Louis: Saunders, 2003; 628-643;
17. Sliver I A, Brown P M, Goodship A R; A Clinical and Experimental Study of Tendon Injury, Healing and Treatment in the Horse. *Equine Veterinary Journal Supplement* 1983; 1: 1-43;
18. Davis C S, Smith R W, Diagnosis and Management of Tendon and Ligament Disorders. In: Aver I. A. Stick J A, eds. Equine Surgery 3rd edition St. Louis: Saunders, 2006; 1086-1111;
19. Chesan A B, Dabarciner R M, Chaffin M. Carter G K. Tendonitis of the Proximal Aspect of the Superficial Flexor Tendon in Horses: 12 cases (2000-2006) JAVMA Jun. 1, 2009, Volume 234, November 11 1432-1436;
20. Szabo R, Langa V. Klein M. The Inhibition of Flexor Tendon Adhesions. Bull Hosp JT Dis Orthopedic Institute; 1986 Spring; 46 (1); 16-21;
21. Robinson R J, Brown J W, Deschner W B, Highes B, King H., Annual of Thoracic Surg. 1984 June; 37 (6): 488-490;
22: Eriksson M. Saldeen T; Effect of Dextran on Plasma Tissue Plasminogen Activator (T-PA) and Plasminogen Activator Inhibitor-1 (PAT-1) During Surgery. *Acta Anesthesiol Scand.* 1995 February; 39 (2): 163-166; and
23. Smith R K W, Ultronographic Imaging of the Flexor Tendons in a Clinical Context, *Proceedings of the 10th International Congress of World Equine Veterinary Association, Jan.* 23-Feb. 1, 2008 Moscow Russia. Pg 269-273.

What is claimed is:

1. A composition capable of synergistically attenuating platelet hyperactivation and enhancing connective tissue regeneration comprising:
    a glycosaminoglycan with a weight average molecular weight from about 1.5 to about 6000 kD, and a concentration of about 0.1% to about 7.0%;
    a neutral colloidal polysaccharide with a weight average molecular weight of about 20 to about 75 kD, and a concentration of about 1.0% to about 25%;
    an isomaltose oligomer with a weight average molecular weight of about 0.4 to about 8 kD, and a concentration of about 0.3% to about 25%;
    wherein the composition is an aqueous parenteral solution.

2. The composition of claim 1, wherein the glycosaminoglycan is selected from at least one of hyaluronan, chondroitin, dermatin, keratin, heparan, heparin, and GAG analogues dextran sulfate, pentosan sulfate, and wherein the neutral colloidal polysaccharide is selected from at least one of dextran, a hydroxyethyl starch and fucoidan.

3. The composition of claim 1, wherein the glycosaminoglycan is hyaluronan, and the neutral colloidal polysaccharide is dextran.

4. The composition of claim 1, wherein the glycosaminoglycan is a partially cross-linked hyaluronan having a degree of cross-linking that is less than about 25%.

5. The composition of claim 1, further comprising at least one of an antioxidant, a scavenger, a cytokine, a growth factor, an interleukin, a gene therapy agent, a viscoelastic agent and a stem cell.

* * * * *